US010441603B2

(12) United States Patent
Koenig et al.

(10) Patent No.: US 10,441,603 B2
(45) Date of Patent: *Oct. 15, 2019

(54) SYNERGISTIC PREBIOTIC COMPOSITION

(71) Applicant: Kimberly-Clark Worldwide, Inc., Neenah, WI (US)

(72) Inventors: David William Koenig, Menasha, WI (US); Michael Andrew Zawadzki, Appleton, WI (US); Cathleen Mae Uttecht, Menasha, WI (US); Jeffrey Janne Johnson, Neenah, WI (US); David Andrew Moline, Appleton, WI (US); Rebecca Ann Vongsa, Neenah, WI (US); Amy Lynn Vanden Heuvel, Hortonville, WI (US); YoungSook Kim, Yongin-Si (KR); SangHa Park, Yongin-Si (KR); Jessica Caroline Rogers, Appleton, WI (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 99 days.

This patent is subject to a terminal disclaimer.

(21) Appl. No.: 15/512,951

(22) PCT Filed: Sep. 30, 2014

(86) PCT No.: PCT/US2014/058369
§ 371 (c)(1),
(2) Date: Mar. 21, 2017

(87) PCT Pub. No.: WO2016/053308
PCT Pub. Date: Apr. 7, 2016

(65) Prior Publication Data
US 2017/0258823 A1  Sep. 14, 2017

(51) Int. Cl.
| A61K 31/733 | (2006.01) |
| B31F 1/12 | (2006.01) |
| D21H 27/00 | (2006.01) |
| A61K 31/702 | (2006.01) |
| A61K 31/194 | (2006.01) |
| A61K 45/06 | (2006.01) |
| A61K 31/191 | (2006.01) |
| A61K 9/70 | (2006.01) |
| A61K 31/19 | (2006.01) |
| A61K 47/26 | (2006.01) |
| A61P 1/00 | (2006.01) |
| A61P 17/00 | (2006.01) |
| A61P 43/00 | (2006.01) |

(52) U.S. Cl.
CPC ......... *A61K 31/733* (2013.01); *A61K 9/7007* (2013.01); *A61K 31/19* (2013.01); *A61K 31/191* (2013.01); *A61K 31/194* (2013.01); *A61K 31/702* (2013.01); *A61K 45/06* (2013.01); *A61K 47/26* (2013.01); *A61P 1/00* (2018.01); *A61P 17/00* (2018.01); *A61P 43/00* (2018.01)

(58) Field of Classification Search
CPC .................................................. A61K 31/733
See application file for complete search history.

(56) References Cited

U.S. PATENT DOCUMENTS

| 7,025,974 | B2 | 4/2006 | Farmer et al. |
| 7,332,179 | B2 | 2/2008 | Kistler et al. |
| 7,642,395 | B2 | 1/2010 | Schroeder et al. |
| 8,110,215 | B2 | 2/2012 | Koenig et al. |
| 8,506,978 | B2 | 8/2013 | Soerens et al. |
| 8,552,251 | B2 | 10/2013 | Zhou et al. |
| 9,539,344 | B2 | 1/2017 | Zawadzki et al. |
| 2003/0185811 | A1 | 10/2003 | Teasdale et al. |
| 2004/0226123 | A1* | 11/2004 | Policicchio ............ A47L 13/20 15/115 |
| 2005/0112239 | A1 | 5/2005 | Rudin et al. |
| 2007/0036776 | A1 | 2/2007 | Reid et al. |
| 2007/0178202 | A1 | 8/2007 | Verbruggen et al. |
| 2007/0275129 | A1 | 11/2007 | Pershad et al. |
| 2008/0073046 | A1* | 3/2008 | Dyer .................... A61K 8/0208 162/112 |
| 2008/0206188 | A1 | 8/2008 | Alverdy et al. |
| 2009/0181157 | A1 | 7/2009 | Toreki et al. |
| 2011/0002984 | A1 | 1/2011 | Atkin et al. |
| 2012/0035277 | A1 | 2/2012 | Davis |
| 2012/0058181 | A1 | 3/2012 | Currie et al. |
| 2012/0164200 | A1 | 6/2012 | Qin et al. |
| 2012/0269865 | A1 | 10/2012 | Roughead et al. |
| 2012/0328586 | A1 | 12/2012 | Lang et al. |
| 2013/0004540 | A1 | 1/2013 | O'Mahony et al. |
| 2013/0065967 | A9 | 3/2013 | Benjamin et al. |
| 2013/0137643 | A1 | 5/2013 | Zimmer et al. |
| 2013/0281948 | A1 | 10/2013 | Ehmsperger et al. |
| 2014/0096924 | A1 | 4/2014 | Rekoske et al. |
| 2015/0080826 | A1 | 3/2015 | Ehmsperger et al. |
| 2015/0209468 | A1 | 7/2015 | Aviles et al. |

FOREIGN PATENT DOCUMENTS

| CN | 102370598 A | 3/2012 |
| CN | 102871921 A | 1/2013 |
| DE | 2738652 A1 | 3/1979 |
| GB | 2495491 A1 | 4/2013 |
| WO | WO 2004/017979 A2 | 3/2004 |
| WO | WO 2005/115171 A1 | 12/2005 |
| WO | WO 2010/123419 A1 | 10/2010 |
| WO | WO 2012/118535 A1 | 9/2012 |

* cited by examiner

*Primary Examiner* — Adam C Milligan
*Assistant Examiner* — Sarah Alawadi
(74) *Attorney, Agent, or Firm* — Kimberly-Clark Worldwide, Inc.

(57) ABSTRACT

The present invention relates to prebiotic compositions and formulations comprising an α-hydroxy acid and salts thereof, such as lactic, glycolic, citric, tartaric or malic acid and a prebiotic agent, such as inulin, fructo-oligosaccharide (FOS), lactulose, galacto-oligosaccharide (GOS), raffinose, stachyose, isomalto-oligosaccharide, and xylo-oligosaccharide. Prebiotic compositions of the present invention provide a surprisingly synergist prebiotic effect and may be administered in several forms to a user, such as by application to a premoistened wiping substrate or dry bath tissue.

10 Claims, No Drawings

SYNERGISTIC PREBIOTIC COMPOSITION

BACKGROUND OF THE DISCLOSURE

Prebiotics, which increase the in vivo growth rate or activity of healthy bacteria, often referred to as probiotic bacteria, such as *Bifidobacterium* spp. and *Lactobacillus* spp., are generally soluble fiber sources. Prebiotics have been administered to humans and animals to support intestinal health. Soluble fiber prebiotics are not digested by host animal digestive enzymes but rather, are the energy source for the probiotic species and are digested by enzymes produced by the probiotic species. Soluble fiber prebiotics enhance probiotic growth but are not required for growth.

Although various prebiotic compositions are known in the art there remains a need for more effective prebiotic compositions which support the growth of healthy bacteria in a synergistic manner. Therefore, the object of the present invention is to provide a new prebiotic composition having a synergistic stimulation of the growth of healthy bacteria, preferably *Lactobacillus* and/or *Bifidobacterium* and improves the health status of the human body. A further objective of the present invention is to provide a new prebiotic composition which may be readily applied to a variety of absorbent wiping articles, which may in-turn be used to administer the prebiotic composition to a user's skin.

SUMMARY OF THE DISCLOSURE

It has now been surprisingly discovered that the benefits of a prebiotic may be synergistically increased by combining a prebiotic agent along with at least one α-hydroxy acid. Surprisingly the combination of a prebiotic agent and an α-hydroxy acid synergistically promotes the growth of healthy bacteria such as *Bifidobacterium* spp. or *Lactobacillus* spp. For example, prebiotic compositions of the present invention synergistically promote the growth of at least some strains of Lactobacilli, such as *Lactobacillus gasseri* and *Lactobacillus crispatus*, without promoting growth of enteropathogenic bacteria, such as *Staphylococcus aureus*, particular strains of *Escherichia coli* (*E. coli*), and *Salmonella* spp.

In certain aspects the present invention provides prebiotic formulations for administration to a user. Suitable formulations may include, for example, liquids, solutions, pastes or gels. Accordingly, in one embodiment the present invention provides a prebiotic formulation comprising a prebiotic agent, from about 0.01 to about 5.0 percent, by weight of the formulation, α-hydroxy acid and a solvent, wherein the formulation is a liquid, a solution, a paste or a gel.

In other embodiments the present invention provides a formulation comprising a prebiotic agent selected from the group consisting of inulin, fructo-oligosaccharide (FOS), lactulose and galacto-oligosaccharide (GOS), from about 0.01 to about 1.0 percent, by weight of the formulation, α-hydroxy acid selected from the group consisting of citric acid, lactic acid, methyllactic acid, phenyllactic acid, malic acid, mandelic acid, glycolic acid, tartronic acid, tartaric acid, and water, wherein the ratio to α-hydroxy acid to prebiotic agent is from about 1:100 to about 1:200 and the pH of the formulation is from about 4.0 to about 6.0.

In still other aspects the prebiotic formulations may be applied to an applicator. Suitable applicators include a web, such as a wet laid tissue web or air laid web, gauze, cotton swab, transdermal patch, container or holder. Thus, in certain embodiments the prebiotic composition may be applied to a nonwoven web, such as meltblown, coform, spunbond, airlaid, hydroentangled nonwovens, spunlace, bonded carded webs, and laminates thereof, as well as wet laid fibrous webs, such as tissue webs. Accordingly, in one embodiment the invention provides a prebiotic wipe comprising a nonwoven web and a prebiotic composition disposed thereon, the prebiotic composition comprising a prebiotic agent, from about 0.01 to about 5.0 percent, by weight of the composition, α-hydroxy acid and water.

In yet other embodiments the present invention provides a prebiotic wipe comprising a nonwoven web selected from the group consisting of meltblown, coform, spunbond, airlaid, hydroentangled nonwovens, spunlace and bonded carded webs, the nonwoven web having a basis weight from about 10 to about 100 grams per square meter (gsm), and a prebiotic composition topically applied thereto, the prebiotic composition comprising from about 0.1 to about 10 percent, by weight of the composition, prebiotic agent, from about 0.1 to about 1.0 percent, by weight of the composition, α-hydroxy acid, and from about 89 to about 99 percent, by weight of the composition, water and the composition has a pH from about 4.0 to about 6.0.

In other aspects the prebiotic formulations of the present invention may be administered to a user to provide a prebiotic effect. Accordingly, in one embodiment the present invention provides a method for enhancing *lactobacillus* growth or activity in vivo comprising administering a prebiotic formulation comprising a prebiotic agent, from about 0.01 to about 5.0 percent, by weight of the composition, α-hydroxy acid and water.

DETAILED DESCRIPTION OF THE DISCLOSURE

The present invention is related to prebiotic compositions and formulations comprising at least one α-hydroxy acid and at least one prebiotic agent (also referred to herein simply as a prebiotic), wherein the α-hydroxy acid is present in an amount greater than about 0.01 percent, by weight of the composition or formulation. Prebiotic compositions of the present invention provide a surprisingly synergistic prebiotic effect and may be administered in several forms to a user. For example, the prebiotic compositions may be prepared as formulations for administration to a user or may be applied to a substrate, such as a wiping substrate, for administration to a user.

Surprisingly compositions comprising both a prebiotic agent and an α-hydroxy acid synergistically promote the growth of healthy bacteria such as *Bifidobacterium* spp. or *Lactobacillus* spp. without promoting growth of enteropathogenic bacteria, such as *E. coli*. Accordingly, prebiotic compositions of the present invention may be administered to a user to synergistically and selectively stimulate growth of lactobacilli without stimulating the growth of competing enteropathogenic bacteria. Thus, in-use, administration of a formulation comprising both a prebiotic agent and an α-hydroxy acid may enhance the growth and colonization of healthy bacteria such as *Bifidobacterium* spp. or *Lactobacillus* spp in the user, which thereby helps reduce the incidence of disease.

Prebiotic agents useful in the present invention comprise one or more saccharides (also referred to herein as carbohydrates or sugars) which are non-digestible by a human digestive system. Generally prebiotics stimulate the growth or activity of bacteria in the digestive system of a human upon administration and are beneficial to the health of the human body.

Saccharides that are not digestible by humans and are useful prebiotics within the scope of the present invention include, but are not limited to, transgalactooligosaccharides, galacto-oligosaccharides, lactulose, raffinose, stachyose, lactosucrose, fructo-oligosaccharides, isomalto-oligosaccharides, xylo-oligosaccharides, paratinose oligosaccharides, difructose anhydride III, sorbitol, maltitol, lactitol, reduced paratinose, cellulose, β-glucose, β-galactose, β-fructose, verbascose, galactinol, and β-glucan, guar gum, pectin, high sodium alginate, and lambda carrageenan.

In one embodiment a prebiotic composition comprises a saccharide that is inulin, fructo-oligosaccharide (FOS), lactulose, galacto-oligosaccharide (GOS), raffinose, or stachyose. In a particularly preferred embodiment the prebiotic composition comprises at least one beta-glycosidic (e.g., beta galactosidic or beta glucosidic) bond or at least one bond alpha-glycosidic (e.g., alpha galactosidic or alpha glucosidic) bond, and is non-digestible by a human digestive system, but can be digested by a bacterium. In one embodiment the bacterium is a *Bifidobacterium* spp. or *Lactobacillus* spp.

In other embodiments the prebiotic comprises one or more fructo-oligosaccharides. Fructo-oligosaccharides are generally short-chain oligosaccharides comprised of D-fructose and D-glucose, containing from three to five monosaccharide units. Fructo-oligosaccharides are generally non-digestible and act to stimulate the growth of *Bifidobacterium* spp. or *Lactobacillus* spp.

In one particularly preferred embodiment the prebiotic comprises inulin. Inulin is generally a fructose-containing oligosaccharides and belongs to a class of carbohydrates known as fructans. Inulin comprises fructose units in beta-(2-I) glucosidic linkage and comprises a terminal glucose unit. The average degree of polymerization generally ranges from about ten to about twelve. Inulin stimulates the growth of *Bifidobacterium* spp. or *Lactobacillus* spp.

In still other embodiments the prebiotic comprises one or more isomalto-oligosaccharides. Isomalto-oligosaccharides generally comprise a mixture of alpha-D-linked glucose oligomers including, for example, isomaltose, panose, isomaltotetraose, isomaltopentaose, nigerose, kojibiose, isopanose and higher branched oligosaccharides. Isomaltooligosaccharides generally act to stimulate the growth of *Bifidobacterium* spp. or *Lactobacillus* spp.

In other embodiments the prebiotic comprises one or more xylo-oligosaccharides. Xylo-oligosaccharides are comprised of oligosaccharides containing beta (I→4) linked xylose residues. The degree of polymerization of xylo-oligosaccharides is generally from about two to about four.

Generally compositions of the present invention comprise less than about 10 percent prebiotic, by weight of the composition, and more preferably less than about 5 percent and still more preferably less than about 2 percent, such as from about 0.1 to about 2 percent and more preferably from about 0.5 to about 1 percent, by weight of the composition. For example, in one embodiment, the prebiotic composition comprises from about 0.5 to about 2 percent, by weight of the composition, inulin. In another embodiment the prebiotic composition comprises from about 0.5 to about 1 percent, by weight of the composition, inulin and from about 0.5 to about 1 percent, by weight of the composition fructo-oligosaccharides.

In certain embodiments in addition to comprising a prebiotic the composition may comprise one or more digestible saccharides, such as lactose, glucose or galactose. When present in the composition the digestible saccharide generally comprises less than about 5 percent, by weight of the composition, and more preferably less than about 2 percent and still more preferably less than about 1 percent, such as from about 0.01 to about 1 percent and more preferably from about 0.01 to about 0.5 percent. For example, the composition may comprise a prebiotic selected from the group consisting of galacto-oligosaccharides, fructo-oligosaccharides, isomalto-oligosaccharides, inulin and xylo-oligosaccharides, and from about 0.01 percent to about 2 percent, by weight of the composition, galactose.

In addition to a prebiotic, the compositions of the present invention also comprise at least one α-hydroxy acid. Alpha-hydroxy acids useful in the present invention generally consist of mono- or polycarboxylic acids having one or more hydroxyl functional groups at least one of which is introduced into the α-position (i.e., on the carbon atom adjacent to the carboxyl functional group). Examples of particularly useful α-hydroxy acids include citric acid, lactic acid, methyllactic acid, phenyllactic acid, malic acid, mandelic acid, glycolic acid, tartronic acid, tartaric acid and gluconic acid. In particularly preferred embodiments the α-hydroxy acid is selected from the group consisting of citric acid, lactic acid, malic acid, glycolic acid and tartaric acid.

In the present invention the prebiotic composition may comprise a single α-hydroxy acid or a combination of two or more α-hydroxy acids. For example, in one embodiment the composition comprises lactic acid and an α-hydroxy acid selected from the group consisting of citric acid, methyllactic acid, phenyllactic acid, malic acid, mandelic acid, glycolic acid, tartronic acid, tartaric acid and gluconic acid.

The content of the α-hydroxy acid(s) is preferably sufficient to provide a synergistic prebiotic effect when administered to a user along with a prebiotic agent. Thus, α-hydroxy acid is present in an amount sufficient to stimulate the growth of certain healthy bacteria such as *Bifidobacterium breve, Bifidobacterium infantis, Bifidobacterium longum* and *Bifidobacterium adolescentis* on one hand, and *Lactobacillus bulgaricus, Lactobacillus acidophilus, Lactobacillus gasseri, Lactobacillus crispatus, Lactobacillus casei, Lactobacillus plantarum, Streptococcus faecium*, and *Streptococcus thermophilus* on the other. Accordingly, in certain embodiments, the α-hydroxy acid may range from 0.01 to 2 percent, by weight of the composition, such as from about 0.05 to about 1 percent and more preferably from 0.075 to 0.5 percent and still more preferably from about 0.1 to about 0.25 percent.

The amount of prebiotic agent(s) and α-hydroxy acid(s) may be varied relative to one another. For example, in certain embodiments, the ratio of α-hydroxy acid to prebiotic agent may range from about 1:50 to about 1:1,000, such as from about 1:50 to about 1:500 and more preferably from about 1:100 to about 1:200. Accordingly, in certain embodiments the prebiotic composition may comprises from about 1 to about 10 percent, by weight of the composition, prebiotic agent and from about 0.01 to about 1.0 percent, by weight of the composition, α-hydroxy acid.

In other aspects the compositions may be formulated for administration to a user. Suitable formulations may include, for example, liquids, solutions, pastes or gels. The formulations may be administered to a user as moisturizers, hand and/or body soaps, cosmetics, hand sanitizers, body lotions, and/or other skin products suitable for human use.

Formulations may comprise a prebiotic agent, an α-hydroxy acid, a solvent and optionally a dermatologically acceptable carrier. As used herein, "dermatologically acceptable carrier" generally refers to a carrier that is suitable for topical application to the keratinous tissue and is compatible with a prebiotic. The dermatologically acceptable carrier may be in a wide variety of forms such as, for example, simple solutions (water-based or oil-based), solid forms (e.g. gels or sticks) and emulsions.

Solvents may be either aqueous or non-aqueous. Water is a particularly preferred aqueous solvent. Non-aqueous solvents may include, for example, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the solvent constitutes greater than about 75 percent, by weight of the formulation, more preferably greater than about 85 percent, and still more preferably greater than about 90 percent, such as from about 90 to 99 percent.

In certain embodiments, useful prebiotic formulations may be produced by dissolving the prebiotic agent and α-hydroxy acid in water. Thus, in one preferred embodiment the present invention provides prebiotic formulation comprising a prebiotic agent, an α-hydroxy acid and water, wherein the formulation comprises from about 85 to about 99 percent, by weight of the composition, water.

In addition to the foregoing, useful prebiotic formulations may also contain an emollient, surfactant(s), oils, medicinal agent(s) such as antimicrobial agent(s), fragrance(s), or humectant(s). For example, in one embodiment the composition may comprise one or more surfactants. The surfactant preferably functions to condition the skin. Preferred nonionic surfactant(s) may be selected from the Tween™ or Polysorbate™ family (i.e., based on polyoxyethylene sorbitan fatty acid esters such as the monolaurate), such as Polysorbate 20™. Preferred cationic surfactants are quaternary ammonium compounds. In other embodiments the composition may comprise one or more oils. Suitable oils include, but are not limited to, petroleum or mineral oils, such as mineral oil and petrolatum; plant oils, such as aloe extract, sunflower oil and avocado oil; and silicone oils, such as dimethicone and alkyl methyl silicones. In addition to the foregoing oils, formulations of the present invention may also include an excipient classified as lipids, for example glycerol triacetate, glycerol behenate, glycerol palmitostearate, zinc stearate, magnesium stearate, calcium stearate and stearic acid. Also synthetic lipophilic and amphiphilic ingredients may be used, such as polyethylene glycols (PEG), polyoxyethylene monostearates, sodium lauryl sulphate, and sucrose monolaurate.

The prebiotic formulations of the present invention are generally acidic, i.e., have a pH less than about 7.0 and more preferably less than about 6.0, such as from about 4.0 to about 6.0 and still more preferably from about 4.5 to about 5.0. Thus, in certain embodiments the prebiotic formulation may comprise a prebiotic agent, an α-hydroxy acid and from about 85 to about 98 percent, by weight of the composition, water, wherein the ratio of α-hydroxy acid to prebiotic agent is from about 1:100 to about 1:200 and the pH of the formulation is from about 4.0 to about 6.0.

The prebiotic formulations of the present invention may be applied to a suitable substrate, which in-turn may be used to apply the prebiotic to a user. Suitable applicators include a web, such a wet laid tissue web or air laid web, gauze, cotton swab, transdermal patch, container or holder. Particularly preferred applicators include fibrous webs, including flushable and non-flushable cellulosic webs and nonwoven webs of synthetic fibrous material. Useful webs may be wet laid, air laid, meltblown, or spunbonded. Suitable synthetic fibrous material includes meltblown polyethylene, polypropylene, copolymers of polyethylene and polypropylene, bicomponent fibers including polyethylene or polypropylene, and the like. Useful nonwoven webs may be meltblown, coform, spunbond, airlaid, hydroentangled nonwovens, spunlace, bonded carded webs.

In certain embodiments, particularly those in which the prebiotic formulation is applied to web, it may be desirable that the formulation provide certain physical attributes, such as having a smooth, lubricious, non-greasy feel; the ability to at least partially transfer from the web to the user's skin; the capability to be retained on the web at about room temperature; or the ability to be compatible with the web manufacturing process. In certain embodiments it is preferred that at least a portion of the prebiotic composition is transferred from the tissue to the user's skin in use.

The prebiotic composition may be applied to a web during formation of the web or after the web has been formed and dried, often referred to as off-line or post-treatment. Suitable methods of applying the prebiotic formulation to a web include methods known in the art such as gravure printing, flexographic printing, spraying, WEKO™, slot die coating, or electrostatic spraying. One particularly preferred method of off-line application is rotogravure printing.

In those instances where the prebiotic composition is added to the web during formation of the web and prior to drying, it may be preferred to employ an application method that incorporates the composition on the surface of the web. One method of adding the prebiotic to the web surface is by applying the prebiotic composition during creping of the tissue web. Surprisingly, the prebiotic composition itself may be used as a creping composition or may be combined with other well-known creping compositions to apply the prebiotic composition to a tissue web without significantly degrading important web properties such as strength, stiffness or sloughing.

The preparation of creped tissue webs is well known in the art and generally involves wet forming a fibrous web, partially dewatering the web, pressing the web against a heated cylinder, such as a Yankee dryer, to further dry the web and then removing the web from the drying cylinder with a creping blade. Typically a creping composition comprising an adhesive and/or a release agent is applied to the surface of the creping cylinder to adhere the web. Application of the creping composition is generally by a spray boom adjacent to the rotating drying cylinder.

It has now been discovered that the prebiotic composition may itself be used as a creping composition to adhere the web to the Yankee dryer or may be added to a conventional creping composition. In both instances, whether applied as an additional component of a conventional creping composition or alone, addition of a prebiotic composition at the creping stage of tissue manufacture has proven to be an effective means of applying the prebiotic composition to the surface of a web without negatively affecting other important web properties. In those instances where the prebiotic composition is added to a conventional creping composition, the conventional composition may comprise a polyvinyl alcohol, polyamine-epichlorohydrin resin and/or a cationic polyamidoamine-epichlorohydrin resin. Examples of suitable creping compositions are available under the trade names Crepetrol™ and Rezosol™ (Ashland Water Technologies, Wilmington, Del.).

In other embodiments the creping composition comprises a thermoplastic resin, such as the composition disclosed in U.S. Pat. No. 7,807,023, which is incorporated herein in a manner consistent with the present disclosure. The thermoplastic resin may be contained, for instance, in an aqueous dispersion prior to application to the creping surface. In one particular embodiment, the creping composition may comprise a non-fibrous olefin polymer. The creping composition, for instance, may comprise a film-forming composition and the olefin polymer may comprise a copolymer of ethylene and at least one comonomer comprising an alkene, such as 1 octene. The creping composition may also contain a dispersing agent, such as a carboxylic acid. Examples of particular dispersing agents, for instance, include fatty acids, such as oleic acid or stearic acid.

The creping compositions of the present disclosure are typically transferred to the web at high levels, such that at least about 30 percent of the creping composition applied to the Yankee is transferred to the web, more preferably at least about 45 percent is transferred and still more preferably at least about 60 percent is transferred. Generally from about 45 to about 65 percent of the creping composition applied to the Yankee dryer is transferred to the web. Thus, the amount of creping additive transferred to the sheet is a function of the amount of creping additive applied to the Yankee dryer.

The total amount of creping composition applied to the web can be in the range of from about 0.01 to about 10 percent by weight, based upon the total weight of the web, such as from about 0.1 to about 5 percent by weight, such as from about 0.5 to about 3 percent by weight. To achieve the desired additive application levels the add-on rate of creping composition to the dryer, measured as mass (i.e., mg) per unit area of dryer surface (i.e., $m^2$), may range from about 50 to about 2,000 $mg/m^2$, and still more preferably from about 100 to about 1,200 $mg/m^2$. In a particularly preferred embodiment the creping composition comprises a polyamine-epichlorohydrin resin, a prebiotic and an α-hydroxy acid, which is applied to the Yankee drier at levels from about 100 to about 1,000 $mg/m^2$.

At the foregoing add-on levels creped tissue products of the present invention generally comprise from about 100 to about 2,000 $mg/m^2$ prebiotic, such as from about 500 to about 1,500 $mg/m^2$ and particularly preferably from about 750 to about 1,250 $mg/m^2$. In addition to a prebiotic, the creped tissue products also comprise from about 1 to about 100 $mg/m^2$ α-hydroxy acid, such as from about 10 to about 50 $mg/m^2$ and particularly preferably from about 20 to about 40 $mg/m^2$.

Further, the creping composition may be applied to the paper web so as to cover from about 15 to about 100 percent of the surface area of the web. In certain preferred embodiments the creping composition comprising a prebiotic will cover from about 20 to about 60 percent of the surface area of the web.

Fibrous webs comprising a prebiotic composition made according to the present disclosure can be incorporated into multi-ply products. For instance, in one aspect, a fibrous web made according to the present disclosure can be attached to one or more other fibrous webs to form a wiping product having desired characteristics. The other webs laminated to the fibrous web of the present disclosure can be, for instance, a wet-creped web, a calendered web, an embossed web, a through-air dried web, a creped through-air dried web, an uncreped through-air dried web, an airlaid web, and the like and may or may not comprise a prebiotic.

In one aspect, when incorporating a fibrous web made according to the present disclosure into a multi-ply product, it may be desirable to only apply the creping composition comprising a prebiotic to one side of the fibrous web and to thereafter crepe the treated side of the web. The creped side of the web is then used to form an exterior surface of a multi-ply product. The untreated and uncreped side of the web, on the other hand, is attached by any suitable means to one or more plies.

Tissue webs useful in the present invention generally have a basis weight greater than about 10 gsm, such as from about 10 to about 100 gsm, more preferably from about 20 to about 80 gsm and still more preferably from about 30 to about 60 gsm. At the foregoing basis weights the tissue webs generally have sheet bulks greater than about 3 cubic centimeters per gram (cc/g), such as from about 3 to about 15 cc/g and more preferably from about 5 to about 12 cc/g.

Although the addition of the instant prebiotic composition to a creped tissue product has proven to be particularly advantageous, it should be understood that the prebiotic compositions may be used in combination with other applicators. For example, in certain embodiments the prebiotic compositions of the present invention may be topically applied to a nonwoven web, such as meltblown, coform, spunbond, airlaid, hydroentangled nonwovens, spunlace, bonded carded webs, and laminates thereof, by spraying, printing or the like. Such materials can be comprised of synthetic or natural fibers, or a combination thereof. Typically, the nonwoven fibrous sheet materials have a basis weight of from about 25 to about 120 gsm and in certain preferred embodiments from about 40 to about 90 gsm.

In a particular embodiment, the present invention provides a wipe comprising a prebiotic composition described herein, wherein the wipe comprises a coform basesheet of polymeric microfibers and cellulosic fibers having a basis weight of from about 60 to about 80 gsm and desirably about 75 gsm. Such coform basesheets are manufactured generally as described in U.S. Pat. No. 4,100,324, which is incorporated by reference in a manner consistent with the present disclosure. The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wipes.

Alternatively, the wipes incorporating the prebiotic compositions described herein can comprise a composite, which includes multiple layers of materials such as those described in U.S. Pat. No. 6,028,018, which is incorporated by reference. For example, the wipes may include a three layer composite, which includes an elastomeric film or meltblown layer between two coform layers as described above. In such a configuration, the coform layers may define a basis weight of from about 15 to about 30 gsm and the elastomeric layer may include a film material such as a polyethylene metallocene film.

As mentioned above, one type of applicator suitable for use in combination with the prebiotic compositions is a wet wipe. In addition to the substrate, wet wipes may also comprise a liquid solution. The liquid solution may further include emollients, surfactants, fragrances, preservatives, organic or inorganic acids, chelating agents, pH buffers, or combinations thereof.

The amount of prebiotic composition disposed on, or retained by, a given applicator may vary depending upon the type of material being used, other composition components, such as solvents or surfactants, and the desired end use of applicator. Generally, an applicator will comprise from about 100 to about 2,000 $mg/m^2$ prebiotic, such as from about 500 to about 1,500 $mg/m^2$ and particularly preferably from about 750 to about 1,250 mg/m². In addition to a prebiotic, applicators prepared according to the present invention also comprise from about 1 to about 100 mg/m² α-hydroxy acid, such as from about 10 to about 50 mg/m² and particularly preferably from about 20 to about 40 mg/m².

One particular prebiotic composition useful for applying to an applicator, and particularly a wet wipe, comprises water, an α-hydroxy acid selected from the group consisting of citric acid, lactic acid, methyllactic acid, phenyllactic acid, malic acid, mandelic acid, glycolic acid, tartronic acid, tartaric acid and gluconic acid, a prebiotic selected from group consisting of inulin, fructo-oligosaccharide (FOS), lactulose, galacto-oligosaccharide (GOS), raffinose, stachyose, isomalto-oligosaccharide, and xylo-oligosaccharide, a non-ionic surfactant selected from the Tween™ or Polysorbate™ family (i.e., based on polyoxyethylene sorbitan fatty acid esters such as the monolaurate), such as Polysorbate 20™, and a humectant selected from the group consisting of propylene glycol, glycerin, dipropylene glycol, glyceryl polymethracrylate and glyceryl polymethracrylate. Generally the foregoing composition may comprise from about 0.1 to about 10 percent, by weight of the composition, prebiotic, from about 0.01 to about 1 percent α-hydroxy acid, from about 0.1 to about 1 percent surfactant, and from about 0.1 to about 2 percent humectant.

Test Methods

Prebiotic Effect Protocol

To determine whether a composition has the desired prebiotic effect the effect of a given composition on the ratio of *L. crispatus* to *E. coli* is measured using the following protocol. *Lactobacillus crispatus* (ATCC 33820) is inoculated in Lactobacilli MRS broth and incubated without stirring or shaking and anaerobically at 37° C. *Escherichia coli* K12 (ATCC 29425) is inoculated in Tryptic Soy Broth (TSB) with shaking and aerobically at 37° C.

After overnight incubation the *L. crispatus* is washed twice and re-suspended in PBS and centrifuged at 1,000×g for 3 minutes. Washed cells are diluted 1:10 in PBS to a target of $10^6$ CFU/mL inoculum. After overnight incubation the *E. coli* is washed twice and re-suspended in PBS and centrifuged at 4,000×g for 5 minutes. Washed cells are diluted in a series of 1:10 dilutions in PBS to a target of $10^3$ CFU/mL inoculum.

The extract of dry tissue samples are prepared by placing 10 tissues into a 60-mL syringe with 10 mL PBS. The extract is then filter-sterilized and retained for analysis. Wet or moist wipe samples are prepared by expressing the fluid off the basesheet. The expressed fluid is filter-sterilized and retained for analysis. Approximately 4.5 mL of dry bath tissue extract or 4.5 mL of fluid expressed from moist wipes is added to 14-mL culture tubes (n=3). A positive control is prepared by adding 0.5 mL LAPTgGFree+1% inulinto 14-mL culture tubes (n=3). A negative control is prepared by adding 0.5 mL LAPTgGFree to 14-mL culture tubes (n=3).

One-hundred microliters of *L. crispatus* and *E. coli* inocula are added to the samples and vortexed to mix. The samples are then incubated anaerobically at 37° C. for 24 hours. Samples are then diluted in sterile PBS and plated in duplicate on Lactobacilli MRS agar to enumerate *L. crispatus* colonies and TSA plates to enumerate *E. coli* colonies. Lactobacilli MRS agar plates are incubated anaerobically, and TSA plates are incubated aerobically, at 37° C. for 24 hours. Lactobacilli MRS agar plates are evaluated to determine the viable *L. crispatus* counts and TSA agar plates are evaluated to determine the viable *E. coli* counts. Based upon the counts the $LOG_{10}$ CFU/sample is calculated for each organism for each code.

Examples

Creped Prebiotic Tissue

Inventive sample codes were made using a wet pressed process utilizing a conventional wet pressed pilot scale tissue machine. The sample codes had a target basis weight of about 16.3 gsm. Initially, northern softwood kraft (NSWK) pulp was dispersed in a pulper for 30 minutes at 4 percent consistency at about 100° F. The NSWK pulp was then transferred to a dump chest and subsequently diluted to approximately 3 percent consistency. The NSWK pulp was refined for 8 minutes at about 1 HP-days/MT. The NSWK fibers were added to the middle layer in the 3-layer tissue structure such that NSWK fiber contributed approximately 30 percent of the final sheet weight.

*Eucalyptus* hardwood kraft (EHWK) pulp was dispersed in a pulper for 30 minutes at about 4 percent consistency at about 100° F. The EHWK pulp was then transferred to a dump chest and diluted to about 3 percent consistency. The EHWK pulp fibers were added to dryer and felt layers such that EHWK pulp fibers contributed approximately 70 percent of the final sheet weight.

The wet sheet, about 10 to 20 percent consistency, was adhered to a Yankee dryer through a nip via a pressure roll. The consistency of the wet sheet after the pressure roll nip (post-pressure roll consistency or PPRC) was approximately 40 percent. The wet sheet is adhered to the Yankee dryer due to the creping composition that is applied to the dryer surface. A spray boom situated underneath the Yankee dryer sprayed the creping composition onto the dryer surface. Inulin (BENEO Orafti®HIS, available from BENEO GmbH, Mannheim, Germany) was prepared by dissolving 3071 grams in 60 liters of water (51.2 g Inulin/L). The release agent comprised Crepetrol 874 (Ashland Water Technologies, Wilmington, Del.), which was prepared by dissolving 18.54 g of Crepetrol in 60 liters of water (0.31 g Crepetrol/L). When applied to the Yankee, inulin was added at 849 gsm of dryer surface area and Crepetrol was applied at 5.14 mg per square meter of dryer surface area.

The sheet was dried to about 98 to 99 percent consistency as it traveled on the Yankee dryer and to the creping blade. The creping blade subsequently scraped the tissue sheet and a portion of the creping composition off the Yankee dryer. The creped tissue basesheet was then wound onto a core traveling at about 1575 fpm (480 mpm) into soft rolls for converting. Two soft rolls of the creped tissue were then rewound, calendered, and plied together so that both creped sides were on the outside of the 2-ply structure. Mechanical crimping on the edges of the structure held the plies together. The plied sheet was then slit on the edges to a standard width of approximately 8.5 inches, and cut to facial tissue length.

The ability of the foregoing tissue sample to stimulate the growth of *L. crispatus* and decrease the growth of *E. coli* was assessed using the prebiotic assay described above. Various control samples were also prepared and assessed, as well as a sample containing additional lactic acid. Tissue samples (approximately 1.53 grams) were prepared and subjected to the prebiotic testing protocol described above. In certain instances lactic acid was added to the sample. In those instances where lactic acid was added, 0.5 mL of diluted lactic acid (1.25 mL of 80 percent lactic acid solution diluted to 1 L water) was added to the test sample. The final concentration of lactic acid in the sample was 0.01 percent. The various samples and the results of the prebiotic assay are described in the table below.

TABLE 1

| Sample | Creping Composition | Lactic Acid Addition (mg) | Ratio Inulin:LA | L. crispatus (Avg. CFU/Sample) | E. coli (Avg. CFU/Sample) | Ratio L. crispatus:E. coli |
|---|---|---|---|---|---|---|
| 1 | — | — | — | 522322 | 28254405 | 0.02 |
| 2 | — | 0.61 | — | 39685 | 43569 | 0.9 |
| 3 | Crepetrol 874/Inulin | — | — | 8355253 | 1454 | 5745 |
| 4 | Crepetrol 874/Inulin | 0.61 | 124:1 | 10544784 | 54 | 195778 |

Prebiotic Formulation

To demonstrate the ability of a formulation comprising inulin and lactic acid to enhance the ratio of *L. crispatus* to *E. coli* the following formulation was prepared.

TABLE 2

| Component | Weight Percent |
|---|---|
| Water | 97.54 |
| Lactic Acid | 0.06 |
| Polysorbate 20 | 0.3 |
| Propylene Glycol | 1.0 |
| *Aloe Vera* | 0.01 |
| Ethylhexyl Glycerin | 0.1 |
| Sodium Benzoate | 0.45 |
| Fragrance | 0.04 |

To the formulation above a control was prepared by adding 0.5 weight percent water. An inventive code was prepared by adding 0.5 weight percent inulin (BENEO Orafti®HIS, available from BENEO GmbH, Mannheim, Germany). The formulation had a pH of 4.80. The prebiotic effect of the formulation was then measured using the assay described above in the Test Methods section, the results of which are summarized below.

TABLE 3

| Inulin (wt %) | L. crispatus (Avg. CFU/Sample) | E. coli (Avg. CFU/Sample) | Ratio L. crispatus:E. coli |
|---|---|---|---|
| — | 7.0 | 4.6 | 251.2 |
| 0.5 | 7.7 | <1.4 | >1995262.3 |

In view of the foregoing description and examples, the present invention provides, in a first embodiment, a prebiotic formulation comprising a prebiotic agent, from about 0.01 to about 5.0 percent, by weight of the formulation, an α-hydroxy acid and a solvent, wherein the formulation is a liquid, a solution, a paste or a gel.

The invention further provides, in a second embodiment, the formulation of the first embodiment wherein the weight ratio of α-hydroxy acid to prebiotic agent is from about 1:1 to about 1:1,000.

Still further, the invention provides, in a third embodiment, the formulation of the first or second embodiment, wherein the weight ratio of α-hydroxy acid to prebiotic agent is from about 1:100 to about 1:200 and the pH of the formulation is from about 4.0 to about 6.0.

The invention also provides a fourth embodiment comprising any one of the first, second or third embodiments, wherein the prebiotic agent is selected from the group consisting of inulin, fructo-oligosaccharide (FOS), lactulose, galacto-oligosaccharide (GOS), raffinose, stachyose, isomalto-oligosaccharide, and xylo-oligosaccharide.

The invention further provides a fifth embodiment comprising any one of the first through fourth embodiments, wherein the α-hydroxy acid is selected from the group consisting of citric acid, lactic acid, methyllactic acid, phenyllactic acid, malic acid, mandelic acid, glycolic acid, tartronic acid, tartaric acid and gluconic acid.

Still further, the invention provides a sixth embodiment comprising any one of the first through fifth embodiments, wherein the solvent is selected from water, propylene glycol, butylene glycol, triethylene glycol, hexylene glycol, polyethylene glycols, ethoxydiglycol, dipropyleneglycol ethanol, n-propanol, isopropanol, acetone, triacetin and ethyl acetate.

The invention further provides a seventh embodiment comprising any one of first through sixth embodiments, wherein the formulation comprises from about 0.1 to about 10 percent, by weight of the formulation, prebiotic agent, from about 0.1 to about 1.0 percent, by weight of the formulation, α-hydroxy acid, and from about 89 to about 99 percent, by weight of the formulation, water and the formulation has a pH from about 4.0 to about 6.0.

And further still the invention provides an eighth embodiment comprising a prebiotic wiping substrate and any one of the formulations of the first through seventh embodiments.

The invention also provides a ninth embodiment comprising the wiping substrate of the eighth embodiment, wherein the wiping substrate is a nonwoven material selected from the group consisting of meltblown, coform, spunbond, airlaid, hydroentangled nonwovens, spunlace, bonded carded webs and a tissue web having a basis weight greater than about 10 gsm and a bulk greater than about 3 cc/g, and laminates thereof.

What is claimed is:

1. A prebiotic wipe comprising a wiping substrate and a prebiotic composition disposed thereon, the prebiotic composition comprising from about 0.5 to about 2.0 percent, by weight of the prebiotic composition, a prebiotic agent selected from the group consisting of inulin, fructo-oligosaccharide (FOS), lactulose, galacto-oligosaccharide (GOS), raffinose, stachyose, isomalto-oligosaccharide, and xylo-oligosaccharide, from about 0.01 to about 1.0 percent, by weight of the prebiotic composition, α-hydroxy acid and water, wherein the weight ratio of the α-hydroxy acid to the prebiotic agent is from about 1:100 to about 1:200 and the wipe comprises from about 500 to about 1,500 mg of the prebiotic agent and from about 10 to about 50 mg of the α-hydroxy acid per square meter of wiping substrate.

2. The prebiotic wipe of claim 1 wherein the pH of the prebiotic composition is from about 4.0 to about 6.0.

3. The prebiotic wipe of claim 1 wherein the α-hydroxy acid is selected from the group consisting of citric acid, lactic acid, methyllactic acid, phenyllactic acid, malic acid, mandelic acid, glycolic acid, tartronic acid, tartaric acid and gluconic acid.

4. The prebiotic wipe of claim 1 further comprising a digestible saccharide selected from the group consisting of lactose, glucose and galactose.

5. The prebiotic wipe of claim 1 wherein the prebiotic composition comprises from about 89 to about 99 percent, by weight of the composition, water and the composition has a pH from about 4.0 to about 6.0.

6. The prebiotic wipe of claim 1 wherein the wiping substrate is a nonwoven material selected from the group consisting of meltblown, coform, spunbond, airlaid, hydroentangled nonwovens, spunlace, bonded carded webs, and laminates thereof.

7. The prebiotic wipe of claim 1 wherein the wiping substrate is a tissue web having a basis weight greater than about 10 grams per square meter and a bulk greater than about 3 cubic centimeters per gram.

8. A prebiotic wet wipe comprising a wipe substrate and a liquid prebiotic composition disposed thereon, the prebiotic composition comprising:
  (a) water,
  (b) from about 500 to about 1,500 mg of a prebiotic agent selected from the group consisting of inulin, fructo-oligosaccharide (FOS), lactulose, galacto-oligosaccharide (GOS), raffinose, stachyose, isomalto-oligosaccharide, and xylo-oligosaccharide, per square meter of the wipe substrate;
  (c) from about 10 to about 50 mg of an α-hydroxy acid is selected from the group consisting of citric acid, lactic acid, methyllactic acid, phenyllactic acid, malic acid, mandelic acid, glycolic acid, tartronic acid, tartaric acid, and gluconic acid, per square meter of the wipe substrate;
  (d) a surfactant, and
  (e) a humectant, wherein the weight ratio of the α-hydroxy acid to the prebiotic agent is from about 1:100 to about 1:200.

9. The prebiotic wipe of claim 8 wherein the surfactant is non-ionic and the humectant is selected from the group consisting of propylene glycol, glycerin, dipropylene glycol, glyceryl polymethracrylate and glyceryl polymethracrylate.

10. The prebiotic wipe of claim 8 wherein the prebiotic composition comprises from about 0.1 to about 10 percent the prebiotic agent, from about 0.01 to about 1 percent the α-hydroxy acid, from about 0.1 to about 1 percent the surfactant, and from about 0.1 to about 2 percent the humectant, where all percentages are weight percentages based upon the weight of the prebiotic composition.

* * * * *